United States Patent [19]

Juergens

[11] Patent Number: 4,802,197

[45] Date of Patent: Jan. 31, 1989

[54] MOBILE X-RAY EXAMINATION UNIT

[75] Inventor: Hans Juergens, Erlangen, Fed. Rep. of Germany

[73] Assignee: Siemens Aktiengesellschaft, Berlin and Munich, Fed. Rep. of Germany

[21] Appl. No.: 943,194

[22] Filed: Dec. 18, 1986

[30] Foreign Application Priority Data

Mar. 11, 1986 [DE] Fed. Rep. of Germany ....... 3608041

[51] Int. Cl.$^4$ .............................................. H05G 1/02
[52] U.S. Cl. .................... 378/197; 378/194; 378/198
[58] Field of Search ........................ 378/197, 198, 194

[56] References Cited

U.S. PATENT DOCUMENTS

| 3,617,749 | 11/1971 | Massiot | 378/197 |
| 4,065,978 | 1/1978 | Meresz et al. | |
| 4,150,297 | 4/1979 | Borggren | 378/197 |
| 4,187,429 | 2/1980 | Tomita et al. | 378/197 |

FOREIGN PATENT DOCUMENTS 59144 10/1946 Netherlands .
1175032 12/1969 United Kingdom .

Primary Examiner—Carolyn E. Fields
Assistant Examiner—David P. Porta
Attorney, Agent, or Firm—Hill, Van Santen, Steadman & Simpson

[57] ABSTRACT

The invention relates to a mobile X-ray examination unit including a C-bend that carries an X-radiator and a radiation receiver at its ends and that is displaceably seated on a carriage which includes a horizontally disposed boom, whereby the C-bend is displaceably seated in a holder along its circumference. The holder is arranged on the boom in height-adjustable fashion, preferably via a scissors rodding. The cables for X-radiator and radiation receiver are conducted out of view within the C-bend.

3 Claims, 2 Drawing Sheets

MOBILE X-RAY EXAMINATION UNIT

BACKGROUND OF THE INVENTION

1. Field of the Invention

The invention relates to a mobile X-ray examination unit including a C-bend which carries an X-radiator and a radiation receiver at its ends and is displaceably seated on a carriage which includes a horizontally disposed boom, whereby the C-bend is adjustably guided in a support along its circumference.

2. Description of the Prior Art

X-ray examination units of this type allow a universal adjustment of the X-ray beam path in space and are employed for X-ray monitoring in the execution of operations. The C-bend thereby embraces the body part to be transilluminated.

SUMMARY OF THE INVENTION

An object of the invention is to fashion an X-ray examination unit of the type described above such that both a height adjustment as well as an adjustment of the C-bend along its circumference are enabled by means of a simple mechanism.

This object is achieved in accord with the invention in that the holder for the C-bend is arranged on the boom in height-displaceable fashion. A height adjustment of the C-bend with the X-radiator and the radiation receiver is thus possible by means of a simple height adjustment mechanism between the holder and the boom of the carriage. The height adjustment mechanism can be formed by a scissors rodding or linkage in a simple way.

An especially practical embodiment derives when the cables for the X-radiator and the radiation receiver are conducted in the C-bend, whereby a roll for the opposed winding and unwinding of the cables is provided in the holder. In this execution, cables laid in the open to the X-radiator and to the radiation receiver are eliminated.

BRIEF DESCRIPTION OF THE DRAWINGS

The invention shall be set forth in greater detail below with reference to an exemplary embodiment shown in the drawing. Thereby shown are.

DESCRIPTION OF THE PREFERRED EMBODIMENTS

Figure 1:
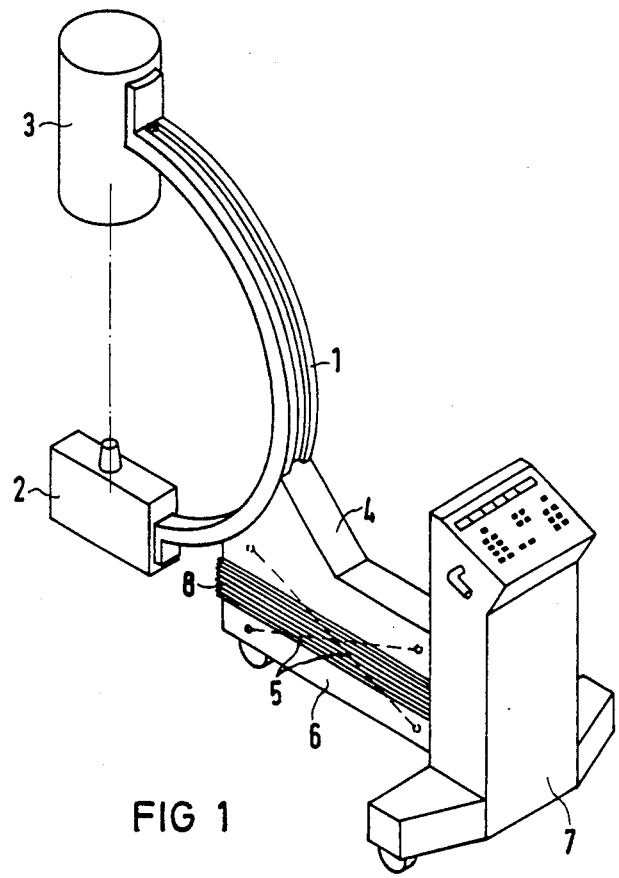
FIG. 1 is a perspective view of an X-ray examination unit embodying the principles of the present invention.

FIG. 1 shows a C-bend 1 which carries an X-radiator 2 and an X-ray image intensifier 3 at its ends. During an X-ray examination, the patient lies between the X-radiator 2 and the X-ray image intensifier 3, i.e. the C-bend 1 thereby embraces the part of the patient's body to be examined. The C-bend 1 is adjustably seated at a holder 4 along its circumference, this holder 4 being connected to a boom 6 of a carriage 7 via a scissors rodding or linkage 5. The carriage 7 carries three wheels for moving the X-ray examination unit on the floor. One of these wheels is provided at the boom 6.

For the adjustment of the X-ray beam path, the C-bend 1 including the X-radiator 2 and the X-ray intensifier 3 is adjustable, first, over its circumference relative to the holder 4 and, second, is adjustable together with the holder 4 relative to the boom 6 and, thus, to the carriage 7, being adjustable in height. The scissors rodding 5 is thereby covered with an accordion sheath 8.

Figure 2:
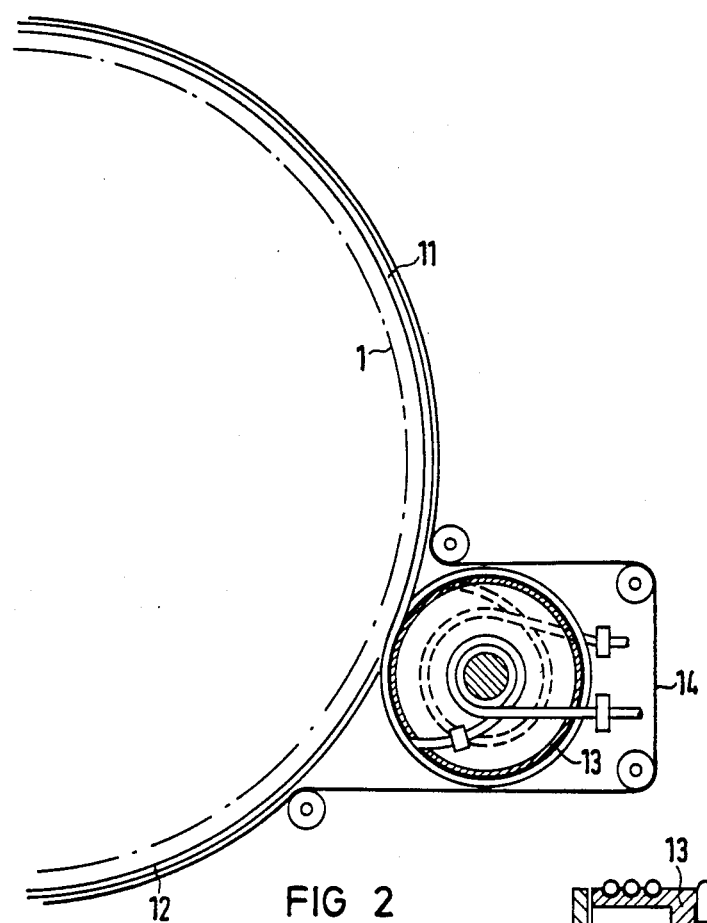
FIG. 2 is a schematic side sectional view of the cable laying of the X-ray examination unit of FIG. 1.
Figure 3:
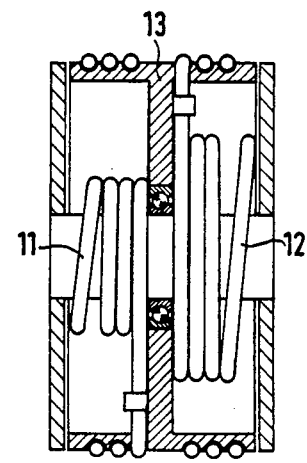
FIG. 3 is a sectional view of the cable drum of FIG. 2.

The cables to the X-radiator 2 and to the X-ray image intensifier 3 are conducted out of sight in the inside of the C-bend 1. FIGS. 2 and 3 show the essential elements of the cable guidance. The C-bend 1 is schematically shown in FIG. 2. The cable 11 leads to the X-ray image intensifier 3 and the cable 12 leads to the X-radiator 2. The cables 11, 12 are oppositely would onto a cable drum 13 which is only schematically shown in FIG. 2. FIG. 3 shows the cable drum 13 in greater detail. The cable drum 13 is mounted in the holder 4. As a consequence of the opposed cable winding, one of the cables 11, 12 unwinds from the cable drum 13 and the other is wound up when the C-bend 1 is adjusted relative to the holder 4. Cable loops thus do not occur in the inside of the unit. FIG. 2 shows that the cable drum 13 is covered toward the outside by a cover band 14 guided over rollers, this band 14 being secured to the C-bend 1.

As is apparent from the foregoing specification, the invention is susceptible of being embodied with various alterations and modifications which may differ particularly from those that have been described in the preceding specification and description. It should be understood that I wish to embody within the scope of the patent warranted hereon all such modifications as reasonably and properly come within the scope of my contribution to the art.

I claim as my invention:

1. A mobile X-ray examination unit including a C-bend that carries an X-radiator and a radiation receiver at its ends and which is displaceably seated on a carriage which includes a horizontally disposed boom, said C-bend being guided in an adjustable fashion in a holder along its circumference, the improvements comprising the holder being directly arranged on the boom and a height-adjustable means being directly connected with the holder and the boom and being formed by a scissors linkage.

2. An X-ray examination unit according to claim 1, which includes a group of cables for the X-radiator and a group of cables for the radiation receiver guided in the C-bend and in the holder, said holder includes a roller for receiving the group of cables with opposite directions of winding so that rotation of the roller causes unwinding of one group and a winding of the other group.

3. A mobile X-ray examination unit including a C-bend that carries an X-radiator and a radiation receiver at its ends and which is displaceably seated on a carriage which includes a horizontally disposed boom, the C-bend being guided in adjustable fashion in a holder along its circumference, the improvements comprising the holder being directly arranged on the boom, a height-adjustable means being directly connected with the holder and the boom, said C-bend receiving a group of cables for the radiation receiver and a group of cables for the X-radiator and said holder including a roller for receiving the groups of cables with opposite directions of windings so that rotation of the roller unwinds one group from the roller as the other group is wound onto the roller.

* * * * *